US010391071B2

(12) United States Patent
Zanella et al.

(10) Patent No.: US 10,391,071 B2
(45) Date of Patent: Aug. 27, 2019

(54) COMPOSITIONS COMPRISING VALERIAN EXTRACTS

(71) Applicant: Cutech SRL, Padua (IT)

(72) Inventors: Lorenzo Zanella, Venezia-Maestre (IT); Michele Massironi, Padua (IT); Paolo Pertile, San Pietro Viminarlo-Padua (IT)

(73) Assignee: CUTECH SRL, Padua (IT)

( * ) Notice: Subject to any disclaimer, the term of this patent is extended or adjusted under 35 U.S.C. 154(b) by 0 days.

(21) Appl. No.: 15/569,676

(22) PCT Filed: Apr. 26, 2016

(86) PCT No.: PCT/EP2016/059251
§ 371 (c)(1),
(2) Date: Oct. 26, 2017

(87) PCT Pub. No.: WO2016/174011
PCT Pub. Date: Nov. 3, 2016

(65) Prior Publication Data
US 2018/0116984 A1    May 3, 2018

(30) Foreign Application Priority Data

Apr. 28, 2015 (EP) .................................. 15165451

(51) Int. Cl.
*A61K 8/37* (2006.01)
*A61K 31/19* (2006.01)
*A61K 36/84* (2006.01)
*A61K 8/36* (2006.01)
*A61Q 5/00* (2006.01)
*A61Q 5/02* (2006.01)
*A61Q 90/00* (2009.01)
*A61K 8/97* (2017.01)
*A61P 17/08* (2006.01)

(52) U.S. Cl.
CPC ............... *A61K 31/19* (2013.01); *A61K 8/36* (2013.01); *A61K 8/97* (2013.01); *A61K 36/84* (2013.01); *A61P 17/08* (2018.01); *A61Q 5/006* (2013.01); *A61Q 5/008* (2013.01); *A61Q 5/02* (2013.01); *A61Q 90/00* (2013.01); *A61K 2800/74* (2013.01)

(58) Field of Classification Search
None
See application file for complete search history.

(56) References Cited

U.S. PATENT DOCUMENTS

| 5,641,480 | A | * | 6/1997 | Vermeer | ................. A61K 8/046 424/70.1 |
| 5,869,540 | A | * | 2/1999 | Smith | ...................... A61K 8/97 424/733 |
| 6,913,770 | B2 | | 7/2005 | Andrews et al. | |

FOREIGN PATENT DOCUMENTS

| EP | 988 856 A2 | 3/2000 | |
| EP | 1 293 554 A1 | 3/2003 | |
| EP | 2 724 750 A2 | 4/2014 | |
| WO | 97/36568 A2 | 10/1997 | |
| WO | WO 200067715 A1 * | 11/2000 | ............... A61K 8/00 |
| WO | WO 2005037242 * | 4/2005 | ............... A61K 8/97 |
| WO | 2005/057244 A1 | 9/2005 | |
| WO | 2009/105824 A1 | 9/2009 | |
| WO | 2010/145010 A1 | 12/2010 | |

OTHER PUBLICATIONS

Ethyl valerate [online] retrieved on Apr. 3, 2018 from:https://pubchem.ncbi.nlm.nih.gov/compound/ethyl_valerate; 1 page. (Year: 2018).*
Pentyl pentanoate [online] retrieved on Apr. 3, 2018 from: http://foodb.ca/compounds/FDB000968; 1 page. (Year: 2018).*
Hair [online] retrieved on Apr. 3, 2018 from: http://www.newworldencyclopedia.org/entry/Hair 2008; 6 pages. (Year: 2008).*
Bayramoglu et al.(Process Biochemistry 2011;46:372-378). (Year: 2011).*
Fiume et al. (International Journal of Toxicology 2012;31(Supplment 2):245S-260S) (Year: 2012).*
English Translation of DE4204255A1 1993 7 pages. (Year: 1993).*
What is Acne? How do I treat Acne? [online] retrieved on Feb. 9, 2019 from: https://www.bioclarity.com/pages/what-is-acne; 16 pages). (Year: 2019).*
Dunn et al. (p. 243 in Chapter 14 of: Dermatologic, Cosmeceutic, and Cosmetic Development: Therapeutic and Novel Approaches; CRC Press; 2007 648 pages). (Year: 2007).*
Real et al, "Variation in the composition of the essential oil of *Valeriana officinals* L. roots from Estonia," Proc. Estonian Acad. Sci. Chem., 2007, vol. 56, No. 2, Jan. 1, 2007, pp. 67-74.

* cited by examiner

*Primary Examiner* — Ernst V Arnold
(74) *Attorney, Agent, or Firm* — Dilworth & Barrese, LLP

(57) ABSTRACT

Suggested is a pharmaceutical composition comprising valerian extracts or their derivatives that is particularly useful for affecting the sebaceous gland metabolism by exerting a relevant activity as regulator of sebum production (sebogenesis) and the subcutis adipocytes metabolism by regulating adipogenesis.

13 Claims, No Drawings

COMPOSITIONS COMPRISING VALERIAN EXTRACTS

FIELD OF INVENTION

The present invention is related to compositions comprising extracts from plants belonging to the genus *Valeriana*, preferably *Valeriana officinalis*, or active ingredient derivatives, in particular valeric acid or valerenic acid, their use for making cosmetic compositions and/or medicaments for modulating the activity of sebaceous glands.

STATE OF THE ART

Sebaceous glands are microscopic exocrine glands found throughout all areas of the skin except the palms of the hands and soles of the feet. They secret a natural oil, called sebum, which participates with the sweat to form the hydrolipidic film that covers the skin. Human sebum is a complex mixture of triglycerides, fatty acids, wax esters, sterol esters, cholesterol, cholesterol esters and squalene. Sebum is involved in epidermal development and barrier maintenance, transporting antioxidants, contributing to mechanical protection, body odour, and generation of pheromones. Sebum is directly involved in hormonal signalling, epidermal differentiation, and protection from ultraviolet (UV) radiation. It helps to reduce skin water loss and modulates composition and proliferation of the natural skin microflora.

There are two types of sebaceous glands, those connected to hair follicles, in pilosebaceous units, and those that exist independently. The overproduction of sebum by sebaceous glands of the scalp is the cause of greasy hair, which is considered a relevant aesthetic problem. Many cosmetic treatments, in the form of medicated shampoos and lotions, are proposed to calm the scalp's overproduction of sebum. However, cosmetics companies continuously ask for new products, especially if obtained from natural ingredients. The seborrhea is involved in the occurrence of dandruff, a disorder of the scalp characterized by patches of abundant and loosely adherent flakes, usually accompanied by itching. This accentuated desquamation of the scalp can evolve into seborrheic dermatitis, which appears as a severe form of dandruff accompanied by inflammation and erythema. The etiology of dandruff and seborrheic dermatitis appears to be dependent upon three factors: sebaceous gland secretions, microfloral metabolism, and individual susceptibility. Regulation of the sebum production is therefore a pivotal issue for the prevention of dandruff and seborrheic dermatitis, and the present invention is related, among other things, with this problem.

Undesirable hyperactivity of sebaceous glands can also occur in other parts of the body, especially on the face. Here the overproduction of sebum gives the skin a shiny and aesthetically undesirable appearance (oily skin) and can promote other slight blemishes, such as comedones. In some cases, more serious disorders can occur in the presence of excessive sebum, such as acne, a skin disease characterized by an inflammatory process of the hair follicle and annexed sebaceous gland. *Propionibacterium acnes* is considered to be the infectious agent in acne.

*P. acnes* are aerotolerant anaerobic bacteria which live deep within follicles and pores, using sebum, cellular debris and metabolic byproducts from the surrounding skin tissue as their primary sources of energy and nutrients. Elevated production of sebum by hyperactive sebaceous glands or blockage of the follicle can favour *P. acnes* bacteria proliferation, causing the inflamed pustules (pimples) characteristic of acne. As a consequence, the cosmetics industry is strongly interested in acquiring compounds suited to inhibiting sebum production, especially if this activity is combined with anti-inflammatory properties.

Lastly, compounds suited to regulating sebum production can also find application in products for intimate hygiene, since the female external genitals have many sebaceous glands. Mons pubis, labia majora, labia minora and the external side of the vaginal vestibule are rich in sebaceous glands and their sebum secretion interacts with the bacterial microflora, regulating the pH of the genital area. Fresh sebum does not contain a relevant quantity of free fatty acids, but these are released as an effect of the lipases produced by bacteria, inducing the acidification of the genital environment. The regulation of sebum can therefore prevent alterations to the genital microflora, irritations, itching, etc.

Another aspect of body care that is of interest for the present invention is the modulation of hypodermal adipocytes that are organized in the subcutis. Modulation of the lipid metabolism can be of primary importance for improving personal appearance. Many people suffer from an excessive accumulation of body fat with serious consequences not only on their looks and social relationships, but also on their health and life expectancy. There are few solutions to this apart from rigorous slimming diets, fatiguing exercises, or dangerous and invasive operations of aesthetic surgery. In addition, people of normal weight can also be affected by localised fat deposition in the skin subcutis of particular body regions. Cellulite, for instance, is a typical problem related to this unbalanced fat metabolism, scientifically defined as "lipodystrophy" or "edematous-fibrosclerotic panniculopathy". Very few cosmetic treatments are presently available for reducing the subcutaneous fatty layer, also referred to as subcutis. An excessive accumulation of abdominal fat is another typical aesthetic problem. The cosmetics industry is therefore very interested in the discovery of effective compounds that can prevent the general accumulation of fat in the body, as well as promote lipolysis in the subcutaneous skin tissue.

However, while fat tissue is usually related with aesthetic problems when its presence is excessive, it can also represent a valuable resource to improve the physical appearance. In fact, a moderate amount of hypodermic fat can confer a desirable roundness or turgidity to some parts of the body. When someone wants to substantially remodel their body, they turn to aesthetic surgery to obtain a redistribution of fat by means of injections or autografting interventions. This allows, for instance, augmentation to be obtained in the volume of breasts or buttocks, but this kind of intervention can also be adopted in order to obtain moderate modification of specific parts of the face, such as lips and cheekbones. The interventions on facial regions can, as an alternative, be performed by administering several micro-injections of natural fillers, such as collagen or hyaluronic acid, in order to re-establish the fullness and plumpness typical of young skin. However, the skin problems related with this kind of surgery have to be regarded as typical effects of aging and should preferably be treated by preventing or delaying their occurrence. In fact, it is presently accepted that depletion of the hypodermic fat tissue, also known as lipoatrophy, plays a relevant role in skin aging. In people with normal metabolism of lipids, aging substantially changes the natural distribution of fat within the body, increasing the perivisceral deposits and inhibiting the metabolism of the hypodermic layers, especially on the face, arms and legs. Of course, a reduction in the hypodermal fat layer (subcutis), substantially contributes to modifying the appearance of the skin and might produce undesirable changes in the body contours, especially on the face. Although aesthetic surgery can offer drastic solutions to some of these problems, as previously said, most people do not want to undergo interventions like these, which are expensive and not devoid of risks, such as unwanted reactions or unsatisfactory results. The cosmetics industry is therefore strongly interested in the discovery of natural ingredients that can delay the physiological reduction of the hypodermal fat.

The problem underlying the present invention has therefore been that of providing highly active species obtainable from renewal resources, preferably of plant origin, capable of affecting the sebaceous gland metabolism and suitable for preventing, fighting and curing the various dysfunctions of human skin and hair that are associated therewith.

DESCRIPTION OF THE INVENTION

A first object of the present invention is related to a composition, particularly a pharmaceutical composition and preferably a medicament comprising valerian extracts or their derivatives Further embodiments of the present invention cover a medicament comprising valerian extracts or their derivatives for use in the prevention or treatment of
  dysfunction of human hair and/or skin.
  scalp disorders caused by excessive sebogenesis.
  dandruff.
  seborrhea.
  acne vulgaris.
  comedones.
  metabolic disorders of the hypodermal fat In a preferred embodiment the valerian extracts or their derivatives in these medicaments are either pentanoic acid, valerenic acid or their mixtures. The extracts or derivatives should be present in amounts of about 0.000001 to about 20%, more particularly 0.5 to 4% b.w. and preferably about 1 to about 2% b.w.—calculated on the total medicament.

Surprisingly, it has been observed that valerian extract and its derivatives, in particular valerenic acid and/or pentanoic acid, preferably in a molar ratio of from about 10:90 to about 90:10, more preferably about 25:75 to 75:25 and most preferred about 40:60 to about 60:40 affect the sebaceous gland metabolism by exerting a relevant activity as regulators of sebum production (sebogenesis) and the subcutis adipocytes metabolism by regulating adipogenesis.

The present invention is the result of a major research effort aimed to discover innovative natural ingredients or extracts suitable to offer natural and safe solutions to some of the skin problems mentioned hereinafter.

The experimental results, exemplified hereinafter, have shown that valerian extract and its derivatives can significantly reduce the production of sebum and represent effective active agents for fighting sebum overproduction and the related aesthetic problems, as well as skin and hair follicle disorders.

In a distinct set of experiments performed on ex-vivo full thickness skin samples with subcutis, it has been shown that the same compounds can also modulate the metabolism of adipocytes.

The valerian extracts and their derivatives, in particular valerenic acid and/or pentanoic acid, are mixtures or compounds suitable to be exploited as regulators of sebogenesis and adipogenesis for cosmetic and therapeutic purposes.

Medicaments Comprising Valerian Extracts

Valerian is a commonly used herbal medicinal product for the treatment of anxiety and insomnia. The active extract can be obtained from the whole plant, but active compounds are specially concentrated in its root. It is known that the sedative and anxiolytic effect of valerian is due to its content of compounds active on the gamma-aminobutyric acid (GABA) receptors. GABA is the main inhibitory neurotransmitter in the mammalian central nervous system. There are three major GABA receptors, termed $GABA_A$, $GABA_B$ and $GABA_C$. $GABA_A$ and $GABA_C$ receptors are oligomeric Cl⁻ channels, whereas $GABA_B$ receptors are transmembrane receptors coupled with G-proteins and activate second messenger systems that modulate Ca2+ and K+ ion channels. The binding between GABA and its receptor ends with the catabolization of the neurotransmitter mediated by GABA transaminase enzyme (GABA-T), which catalyzes the conversion of 4-aminobutanoic acid and 2-oxoglutarate into succinic semi-aldehyde and glutamate.

Interestingly, valerian extract comprises at least two compounds significantly involved in this post-synaptic reaction:
  (i) valerenic acid (VA), which acts as allosteric modulator of the $GABA_A$ receptor, and
  (ii) pentanoic acid (PA), which inhibits the GABA-T activity, prolonging the action of GABA on its receptor.

Pentanoic acid is also known under the names butane-1-carboxylic acid, valerianic acid, valeric acid.

Valerian extract contains also other compounds with biological activities similar to valerenic acid: e.g. hydroxyvalerenic acid and acetoxyvalerenic acid. Derivatives with similar activity also include esters obtained from the combination of the cited acids with lower aliphatic alcohols, and represented in particular by ethyl valerate and pentyl pentanoate.

Valerenic acid (VA) is one of the most active compounds in valerian. The anti-anxiety potential of VA has been verified to be mediated by the $GABA_A$ receptors (Khom et al., 2007, *Neuropharmacology* 53: 178-187). The β33 subunits of the receptor are the specific molecular regions involved in the mechanism of action. However, the biological activity of valerian extract and its components is not yet fully understood. For instance, they show a significant affinity for the serotonin receptor ($5-HT_{5a}$), which is well known to modulate sleep-wake cycles and circadian rhythms in the human brain via a G-protein-coupled receptor family (Dietz et al., 2005, *Molecular Brain Research* 138: 191-197).

So far, valerian extract and its derivatives have been exploited in many cosmetic applications, for most of which the mechanism of action is still unknown. WO 1997 036568 A2 (SMITH) disclosed the reduction of skin wrinkles unexpectedly observed as an effect of the mere ingestion of valerian tea on a daily basis. The aqueous valerian root extract was reported as preferential herbal agent for improving the appearance of the skin.

In JP 61 215318 A (SHISEIDO), valeric acid was included among the suggested ingredients of a composition formulated for preventing skin discoloration and lowering UV-absorptivity.

On the other side, the excellent skin whitening and pigmentation inhibitory effect of Valerian coreana extract was also proposed in KR 10 0825 835 B1 (AMOREPACIFIC).

EP 1675564 A1 (SCHWARZKOPF) discloses compositions, containing a valerian extract, for cleaning and soothing the skin of the user.

CN 103 933 359 A (WANG PING PING) refers to a pharmaceutical composition for dispelling keloids, containing, among the other things, valerian root.

Other relevant applications of valerian extract in cosmetics are hair care and hair loss prevention. JP 01 246211 A (POLA) proposed extracts from some kinds of herbs, including the extract obtained from the root of *Valeriana officinalis*, as effective agents to stimulate the metabolism of hair roots and enhance blood circulation around the hair roots.

Also JP 2005 200383 A (SHISEIDO) describes new hair-growing compositions comprising several herbal derivatives, including valerian oil. This latter is known to contain up to 0.9% valerenic acid and 1.2% isovaleric acid (Raal et al., 2007, *Proc. Estonian Acad. Sci. Chem.* 56: 67-74).

Interestingly, a possible mechanism of action as hair protector was provided in 1985, when JP 60 146829 A (ROHTO PHARMA) disclosed the testesterone 5alpha-reductase inhibiting action of numerous plant extracts, including valerian.

Cosmetic or Dermatological Compositions

Another object of the present invention relates to a cosmetic or dermatological composition comprising valerian extracts or their derivatives and a cosmetically acceptable carrier. Preferably the valerian extracts or their derivatives are either pentanoic acid, valerenic acid or their mixtures.

Preferably the cosmetically acceptable carrier is selected from the group consisting of water, C1-C4 aliphatic alcohols, polyols or oil bodies. Typical examples for aliphatic alcohols encompass ethanol, propanol, isopropyl alcohol, and the butanol isomers. Examples for suitable polyols comprise glycerol, ethylene glycol, propylene glycol, diethylene glycol and dipropylene glycol. Suitable oil bodies are described below.

Preferably the valerian extracts or their derivatives are present in said compositions in an amount of about 0.000001 to about 20% b.w., more preferably 0.2 to about 4% b.w. and most preferably about 0.5 to about 3% b.w.—calculated on the total composition.

The preferred cosmetic or dermatological composition of the present invention represents a personal care, hair care, skin care or sun care composition, for example in the form of a cream, lotion, spray, ointment, emulsion, mousse, foam or stick. More preferably the compositions represent a skin cream, skin lotion or hair shampoo.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{81/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkyl-aminopropionic acids and alkylaminoacetic acids containing around 8 to 18 carbon atoms in the alkyl group. Particularly preferred ampholytic surfactants are N-cocoalkylamino-propionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin deriva-tives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacryl-amide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in *Cosm. Toil.* 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) that are liquid or crystalline at room temperature and are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consistiung of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivativesand indole derivatives.

In addition, it is advantageous to combine compounds of formula (I) with active ingredients which penetrate into the skin and protect the skin cells from inside against sunlight-induced damage and reduce the level of cutaneous matrix metalloproteases.

Preferred respective ingredients, so called arylhydrocarbon receptor antagonists, are described in WO 2007/128723, incorporated herein by reference. Preferred is 2-benzylidene-5,6-dimethoxy-3,3-di methyli nda n-1-one.

The UV filters cited below which can be used within the context of the present invention are preferred but naturally are not limiting.

UV filters which are preferably used are selected from the group consisting of
  p-aminobenzoic acid
  p-aminobenzoic acid ethyl ester (25 mol) ethoxylated (INCI name: PEG-25 PABA)
  p-dimethylaminobenzoic acid-2-ethylhexyl ester
  p-aminobenzoic acid ethyl ester (2 mol) N-propoxylated
  p-aminobenzoic acid glycerol ester
  salicylic acid homomenthyl ester (homosalates) (Neo Heliopan® HMS)
  salicylic acid-2-ethylhexyl ester (Neo Heliopan® 05)
  triethanolamine salicylate
  4-isopropyl benzyl salicylate
  anthranilic acid menthyl ester (Neo Heliopan® MA)
  diisopropyl cinnamic acid ethyl ester
  p-methoxycinnamic acid-2-ethylhexyl ester (Neo Heliopan® AV)
  diisopropyl cinnamic acid methyl ester
  p-methoxycinnamic acid isoamyl ester (Neo Heliopan® E 1000)
  p-methoxycinnamic acid diethanolamine salt
  p-methoxycinnamic acid isopropyl ester
  2-phenylbenzimidazole sulfonic acid and salts (Neo Heliopan® Hydro)
  3-(4'-trimethylammonium) benzylidene bornan-2-one methyl sulfate
  beta-imidazole-4(5)-acrylic acid (urocanic acid)
  3-(4'-sulfo)benzylidene bornan-2-one and salts
  3-(4'-methyl benzylidene)-D,L-camphor (Neo Heliopan® MBC)
  3-benzylidene-D,L-camphor
  N-[(2 and 4)-[2-(oxoborn-3-ylidene) methyl]benzyl] acrylamide polymer
  4,4'-[(6-[4-(1,1-dimethyl)aminocarbonyl) phenylamino]-1,3,5-triazine-2,4-diyl)diimino]-bis-(benzoic acid-2-ethylhexyl ester) (Uyasorb® HEB)
  benzylidene malonate polysiloxane (Parsol® SLX)
  glyceryl ethylhexanoate dimethoxycinnamate
  dipropylene glycol salicylate
  tris(2-ethylhexyl)-4,4',4"-(1,3,5-triazine-2,4,6-triyltriimino)tribenzoate (=2,4,6-trianilino-(p-carbo-2'-ethylhexyl-1'-oxy)-1,3,5-triazine) (Uyinu®T150).

Broadband filters which are preferably combined with one or more compounds of formula (I) in a preparation according to the present invention are selected from the group consisting of
  2-ethylhexyl-2-cyano-3,3-diphenyl acrylate (Neo Heliopan® 303)
  ethyl-2-cyano-3,3'-diphenyl acrylate
  2-hydroxy-4-methoxybenzophenone (Neo Heliopan® BB)
  2-hydroxy-4-methoxybenzophenone-5-sulfonic acid
  dihydroxy-4-methoxybenzophenone
  2,4-dihydroxybenzophenone
  tetrahydroxybenzophenone
  2,2'-dihydroxy-4,4'-di methoxybenzophenone
  2-hydroxy-4-n-octoxybenzophenone
  2-hydroxy-4-methoxy-4'-methyl benzophenone
  sodium hydroxymethoxybenzophenone sulfonate
  disodium-2,2'-dihydroxy-4,4'-dimethoxy-5,5'-disulfobenzophenone
  phenol, 2-(2H-benzotriazol-2-yl)-4-methyl-6-(2-methyl-3 (1,3,3,3-tetramethyl-1-(trimethylsilypoxy)disiloxyanyl)propyl) (Mexoryl®XL)
  2,2'-methylene bis-(6-(2H-benzotriazol-2-yl)-4-1,1,3,3-tetramethylbutyl) phenol) (Tinosorb® M)
  2,4-bis-[4-(2-ethylhexyloxy)-2-hydroxyphenyl]-1,3,5-triazine
  2,4-bis-[{(4-(2-ethylhexyloxy)-2-hydroxy}phenyl]-6-(4-methoxyphenyl)-1,3,5-triazine (Tinosorb® S)
  2,4-bis-[{(4-(3-sulfonato)-2-hydroxypropyloxy)-2-hydroxy}phenyl]-6-(4-methoxyphenyl)-1,3,5-triazine sodium salt
  2,4-bis-[{(3-(2-propyloxy)-2-hydroxypropyloxy)-2-hydroxy}phenyl]-6-(4-methoxyphenyl)-1,3,5-triazine
  2,4-bis-[{4-(2-ethylhexyloxy)-2-hydroxy}phenyl]-6-[4-(2-methoxyethyl carbonyl) phenylamino]-1,3,5-triazine 2,4-bis-[{4-(3-(2-propyloxy)-2-hydroxypropyloxy)-2-hydroxy}phenyl]-6-[4-(2-ethylcarboxyl) phenylam- ino]-1,3,5-triazine 2,4-bis-[{4-(2-ethylhexyloxy)-2-hydroxy}phenyl]-6-(1-methylpyrrol-2-yl)-1,3,5-triazine 2,4-bis-[{4-tris-(trimethylsiloxysilylpropyloxy)-2-hydroxy}phenyl]-6-(4-methoxyphenyl)-1,3,5-triazine 2,4-bis-[{4-(2"-methylpropenyloxy)-2-hydroxy}phenyl]-6-(4-methoxyphenyl)-1,3,5-triazine 2,4-bis-[{4-(1',1',1',3',5',5',5'-heptamethylsiloxy-2"-methylpropyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of 4-isopropyl dibenzoyl methane terephthalylidene dibornane sulfonic acid and salts (Mexoryl® SX)

4-t-butyl-4'-methoxydibenzoyl methane (avobenzone)/ (Neo Heliopan® 357)

phenylene bis-benzimidazyl tetrasulfonic acid disodium salt (Neo Heliopan® AP)

2,2'-(1,4-phenylene)-bis-(1H-benzimidazole-4,6-disulfonic acid), monosodium salt 2-(4-diethylamino-2-hydroxybenzoyl) benzoic acid hexyl ester (Uvinul® A Plus)

indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of p-aminobenzoic acid 3-(4'-trimethylammonium) benzylidene bornan-2-one methyl sulfate salicylic acid homomenthyl ester (Neo Heliopan® HMS)

2-hydroxy-4-methoxybenzophenone (Neo Heliopan® ThB)

2-phenylbenzimidazole sulfonic acid (Neo Heliopan® Hydro)

terephthalylidene dibornane sulfonic acid and salts (Mexoryl® SX)

4-tert-butyl-4'-methoxydibenzoyl methane (Neo Heliopan® 357)

3-(4'-sulfo)benzylidene bornan-2-one and salts 2-ethylhexyl-2-cyano-3,3-diphenyl acrylate (Neo Heliopan® 303)

N-[(2 and 4)-[2-(oxoborn-3-ylidene) methyl]benzyl] acrylamide polymer p-methoxycinnamic acid-2-ethylhexyl ester (Neo Heliopan® AV)

p-aminobenzoic acid ethyl ester (25 mol) ethoxylated (INCI name: PEG-25 PABA)

p-methoxycinnamic acid isoamyl ester (Neo Heliopan® E1000)

2,4,6-trianilino-(p-carbo-2'-ethylhexyl-1'-oxy)-1,3,5-triazine (Uvinul® T150)

phenol, 2-(2H-benzotriazol-2-yl)-4-methyl-6-(2-methyl-3 (1,3,3,3-tetramethyl-1-(trimethylsilypoxy)disiloxanyl) propyl) (Mexoryl® XL)

4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan® MBC)

3-benzylidene camphor salicylic acid-2-ethylhexyl ester (Neo Heliopan® OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb® M)

phenylene bis-benzimidazyl tetrasulfonic acid disodium salt (Neo Heliopan® AP)

2,4-bis-[{(4-(2-ethylhexyloxy)-2-hydroxy}phenyl]-6-(4-methoxyphenyl)-1,3,5-triazine (Tinosorb® S)

benzylidene malonate polysiloxane (Parsol® SLX)

menthyl anthranilate (Neo Heliopan® MA)

2-(4-diethylamino-2-hydroxybenzoyl) benzoic acid hexyl ester (Uvinul® A Plus)

indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (pinus), extracts of vitis species or stilbene derivatives isolated or concentrated therefrom, saxifrage extract, scutelleria extract, grape extract and/or microalgae extract, in particular Tetraselmis suecica Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxya nisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular Isochrysis galbana, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actived

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, ZnSO$_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to aout 10% b.w. based on the total weight of the formulation.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benza midi ne hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, Rubus Fruticosus (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), SynGlycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, Arctium lappa fruit extract, Eriobotrya japonica extract, Genkwanin, N-Methyl-L-serine, (-)-alpha-bisabolol or synthetic alpha-bisabolol such as e.g. Dragosantol and Dragosantol 100 from Symrise, oat glucan, Echinacea purpurea extract and soy protein hydrolysate. Preferred actives are selected from the group consisting of hyaluronic acid and derivatives or salts, retinol and derivatives, (-)-alpha-bisabolol or synthetic alpha-bisabolol such as e.g. Dragosantol and Dragosantol 100 from Symrise, oat glucan, Echinacea purpurea extract, Sinorhizobium Meliloti Ferment Filtrate, Calcium ketogluconate, Alpinia galanga leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, Commiphora species, Rubia species, willow, willow-herb, oats, calendula, arnica, St John's wort, honeysuckle, rosemary, Passiflora incarnata, witch hazel, ginger or Echinacea; preferably selected from the group consisting of extracts or fractions from camomile, Aloe vera, oats, calendula, arnica, honeysuckle, rosemary, witch hazel, ginger or Echinacea, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (-)-alpha-bisabolol and/or synthetic mixed-isomer alpha-bisabolol. If natural (-)-alpha-bisabolol is used, this can also be employed as a constituent of an essential oil or of a plant extract or of a fraction thereof, for example as a constituent of (fractions of) oil or extracts of camomile or of Vanillosmopsis (in particular Vanillosmopsis erythropappa or Vanillosmopsis arborea). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

Trpv1 Antagonists.

Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of Sophora japonica; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name:) Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (Leontodon or Taraxacum), Orthosiphon, Vitex, Coffea, Paullinia, Theobroma, Asiasarum, Cucurbita or Styphnolobium, Serenoa repens (saw palmetto), Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera Chondrus, Gloiopeltis, Ceramium, Durvillea, Glycine max, Sanguisorba officinalis, Calendula officinalis, Hamamelis virginiana, Arnica montana, Salix alba, Hypericum perforatum or Gymnema sylvestre.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [W-S23]), isopulegol or its esters (l-(-)-isopulegol, l-(-)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)-N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 Dalton;
- technical oligoglycerol mixtures with a degree of self-condensation of 1.5 to 10, such as for example technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol,
- sugars containing 5 to 12 carbon atoms, for example glucose or sucrose;
- amino sugars, for example glucamine;
- dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, beta-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

Another object of the present invention is related to a first non-pharmaceutical method for modulating sebum production by administration of valerian extracts or their derivatives to human hair or skin, and a second non-pharmaceutical method for modulating the adipocyte metabolism by administration of valerian extracts or their derivatives to the skin or the scalp. Preferably the valerian extracts or derivatives are either pentanoic acid, valerenic acid or their mixtures. The extracts or their derivatives can be administered either by topical or oral application.

Finally, another object of the present invention covers the use of valerian extracts or their derivatives for the treatment of human hair and/or skin. Preferably the valerian extracts or derivatives are either pentanoic acid, valerenic acid or their mixtures.

EXAMPLES

A. Activity of Valerian Extract and its Derivatives on the Sebaceous Gland Metabolism (hSGs)

The following examples are intended to show the modulation of sebum production exerted by the experimental preparations on human sebaceous glands (hSGs) microdissected and cultivated up to day 6. At the end of the culture time, the sebum is extracted and quantified from each experimental group of hSGs and then normalized by the proteins extracted from the residual hSG material (mg lipids/mg proteins). As a result, the biological activity of the tested compounds is inferred by comparing the lipids/proteins ratio of the treated glands with that of the control group. A detailed methodology is reported in EP14179936.1 (Cutech Srl)

The adopted experimental model is based on the cultivation of ex-vivo hSGs at constant concentrations of valerian extracts or purified derivatives. This experimental condition is not reproducible in vivo since both topical and oral administration produce fluctuating concentrations, depending on the frequency and composition of the treatment. It can therefore be assumed that any effective concentration obtained from the ex-vivo experiments needs to be opportunely increased in the product formulations.

This is especially true for topical preparations, in which only a limited part of the active ingredients reaches the target organ. It is assumed, as a very general indication, that a topical preparation should be formulated with 10-1000 fold the effective concentration detected by means of the experimental model adopted here. The magnitude of the multiplication factor required to obtain an effective formulation mainly depends on the chemical characteristics of the active compound(s), effectiveness of the cosmetic vehicle adopted and the frequency of application suggested.

Examples 1 to 4

Activity of Valerenic acid (VA) on Human Sebaceous Glands (hSGs)

hSGs were taken from a scalp sample, cultivated for 6 days and treated with valerenic acid (VA) at different concentrations in order to study the dose-response performance of this compound. The control group was cultured in standard medium, whereas a 5 µM Capsaicin treatment was included in the experimental design as positive control. Capsaicin is an active component of chili peppers suitable to inhibit sebogenesis [Tóth et al., 2009, *J. Invest. Derm.* 129: 329-339]. The effect of the treatment was evaluated by assessing the amounts of normalized lipids obtained from the treated groups, i.e. the quantitive ratio beween sebum lipids and proteins extracted from each group of hSGs (mg of lipids/mg of proteins), with respect to the value obtained from the control group. The results were expressed in percentage values, assuming the normalized lipids obtained from the control group as reference value (100%). The results are reported in Table 1.

TABLE 1

Sebum content in hSGs following treatment with VA. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.2 | |
| 0 | Capsaicin | 5 µM | 83.3 | 2.4 | p < 0.01 |
| 1 | VA | 0.05 µM | 98.9 | 1.4 | n.s. |
| 2 | VA | 0.5 µM | 74.2 | 1.6 | p < 0.01 |
| 3 | VA | 5 µM | 88.0 | 1.6 | p < 0.01 |
| 4 | VA | 50 µM | 88.6 | 1.5 | p < 0.01 |

The positive control treatment reduced the sebum content of the hSGs by 17% in comparison with the control group. However, surprisingly, VA produced an intense sebogenesis inhibition between 0.5 and 50 µM. The more intense response was detected following the treatment at 0.5 µM VA, which induced a 26% reduction of sebum content in the hSGs. This inhibition resulted as more intense than that induced by capsaicin. All the responses to treatments with VA at concentrations of between 0.5 µM and 50 µM were highly significant on a statistical basis.

Examples 5 to 7

Activity of Valerenic acid (VA) on Human Sebaceous Glands (hSGs)

The previously described experiment was replicated with hSGs taken from another donor. The results are reported in Table 2.

TABLE 2

Sebum content in hSGs following treatment with VA. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.9 | |
| 0 | Capsaicin | 5 µM | 90.2 | 1.1 | $p < 0.01$ |
| 5 | VA | 0.05 µM | 85.6 | 3.5 | $p < 0.01$ |
| 6 | VA | 0.5 µM | 61.2 | 1.6 | $p < 0.01$ |
| 7 | VA | 5 µM | 88.5 | 1.6 | $p < 0.01$ |

The positive control treatment reduced the hSGs sebum content by 10% in comparison with the control group. However, surprisingly, in this case VA produced a more intense sebogenesis inhibition between 0.05 and 5 µM. These results confirm the biological activity of VA on sebogenesis. The donor responded intensely at the lower treatment and the response started to decrease at the maximal dosage. It is not unusual that the biological response of some tissues disappears or is reversed when a stimulating treatment is overdosed in comparison to the optimal concentration range. These data suggest that the optimal treatment can vary between 0.05 and 5 µM, depending on the sensitivity of the treated subject.

Examples 8 to 9

Activity of Valerenic Acid (VA) on Human Sebaceous Glands (hSGs)

The best performing concentrations of VA, i.e. 0.05 and 0.5 µM, were tested again on hSGs taken from another donor. The results are reported in Table 3.

TABLE 3

Sebum content in hSGs following treatment with VA. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 0.9 | |
| 8 | VA | 0.05 µM | 75.0 | 1.0 | $p < 0.01$ |
| 9 | VA | 0.5 µM | 89.0 | 0.6 | $p < 0.01$ |

The results show that both treatment dosages produced a significant reduction of sebum content in the hSGs, but the better response followed the treatment at 0.05 µM VA.

Examples 10 to 11

Activity of Valerenic Acid (VA) on Human Sebaceous Glands (hSGs)

The best performing concentrations of VA, i.e. 0.05 and 0.5 µM, were tested again on hSGs taken from another donor. The results are reported in Table 4.

TABLE 4

Sebum content in hSGs following treatment with VA. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 0.9 | |
| 0 | Capsaicin | 5 µM | 37.2 | 0.7 | $p < 0.01$ |
| 10 | VA | 0.05 µM | 54.1 | 1.1 | $p < 0.01$ |
| 11 | VA | 0.5 µM | 63.9 | 1.0 | $p < 0.01$ |

The results show that both treatment dosages produced a significant reduction of sebum content in the hSGs, but the better response followed the treatment at 0.05 µM VA.

Examples 12 to 13

Activity of Pentanoic Acid (PA) on Human Sebaceous Glands (hSGs)

Another compound usually present in valerian extracts is pentanoic acid (PA). The biological activity of this molecule was tested on ex-vivo hSGs according to the procedures adopted for the previous experiments. The results are reported in Table 5.

TABLE 5

Sebum content in hSGs following treatment with PA. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.8 | |
| 0 | Capsaicin | 5 µM | 45.6 | 0.4 | $p < 0.01$ |
| 12 | PA | 0.2 mM | 57.3 | 0.9 | $p < 0.01$ |
| 13 | PA | 2 mM | 65.6 | 0.4 | $p < 0.01$ |

The results attested that the treatment with PA induced a significant decrease of sebum in hSGs at both the tested concentrations.

Examples 14 to 21

Comparative Analysis of the Activity of Valerenic Acid (VA) and Pentanoic Acid (PA) on Human Sebaceous Glands (hSGs)

In the experiment reported hereinafter, SGs taken from the same donor were treated with different concentrations of PA, VA and PA+VA (i.e. a treatment including both compounds). The aim was to compare the intensity of action of these two valerian extract derivatives and explore possible synergistic actions between them. The experimental protocol was analogous to the previous ones. The results are reported in Table 6.

TABLE 6

Sebum content in hSGs following treatment with PA, VA and a combination of these compounds. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.1 | |
| 0 | Capsaicin | 5 μM | 59.2 | 0.7 | $p < 0.01$ |
| 14 | PA | 0.02 mM | 62.5 | 0.8 | $p < 0.01$ |
| 15 | PA | 0.2 mM | 60.9 | 1.3 | $p < 0.01$ |
| 16 | PA | 2.0 mM | 75.4 | 0.9 | $p < 0.01$ |
| 17 | VA | 0.05 μM | 41.4 | 0.6 | $p < 0.01$ |
| 18 | VA | 0.5 μM | 50.4 | 0.9 | $p < 0.01$ |
| 19 | VA | 5.0 μM | 70.7 | 1.0 | $p < 0.01$ |
| 20 | PA<br>VA | 0.02 mM<br>0.05 μM | 57.3 | 1.0 | $p < 0.01$ |
| 21 | PA<br>VA | 0.2 mM<br>0.5 μM | 68.1 | 1.1 | $p < 0.01$ |

All the treatments produced a decrease in sebum content, confirming the inhibiting action of the experimental compounds. The most intense response was detected following treatments with VA at 0.05-0.5 μM; however, PA also produced very similar inhibition to capsaicin. From these results, it seems that VA induces a more intense response than PA, despite its concentration being about 1000 fold lower. No synergistic effect was displayed by treatments with both the compounds.

Examples 22 to 25

Activity of Valerian Extract (VE) on Human Sebaceous Glands (hSGs)

The previous experiments were based on the use of some typical compounds obtained from the valerian root extract. However, the product generally used in a pharmacopeia is the whole valerian root extract, which has a complex composition, comprising hundreds of molecules. In the experiment reported hereinafter, SGs taken from a donor were treated with increasing dosage of dry valerian root extract (VE) dissolved in the culture medium. The aim was to verify if the raw extract has the same properties as its main compounds (i.e. VA and PA) or if other molecules included in the extract composition interfere with the inhibition of sebum production.

The experimental protocol was analogous to the previous ones. The results are reported in Table 7.

TABLE 7

Sebum content in hSGs following treatment with valerian root extract (VE). Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.3 | |
| 0 | Capsaicin | 5 μM | 83.0 | 1.4 | $p < 0.01$ |
| 22 | VE | 0.04 μg/ml | 95.3 | 2.0 | n.s. |
| 23 | VE | 0.4 μg/ml | 72.2 | 2.0 | $p < 0.01$ |
| 24 | VE | 4 μg/ml | 80.3 | 1.0 | $p < 0.01$ |
| 25 | VE | 40 μg/ml | 102.5 | 2.1 | n.s. |

The results show that the activity of the VE is consistent with that of VA and PA. The effective dosage ranged between 0.4 and 0.04 μg/ml, producing a 20-28% inhibition of sebum production in comparison with the control. This response is more intense than that produced by the positive control (capsaicin; −17%).

Examples 26 to 27

Activity of Valerian Extract (VE) on Human Sebaceous Glands (hSGs)

This experiment compared the activity of the valerian root extract (VE) with that of valerenic acid (VA). The treatment dosages were defined from the best performing previous treatments.

The experimental protocol was analogous to the previous ones. The results are reported in Table 8.

TABLE 8

Sebum content in hSGs following treatment with valerian root extract (VE). Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.8 | |
| 26 | VE | 4 μg/ml | 81.1 | 1.8 | $p < 0.01$ |
| 27 | VA | 0.5 μM | 71.4 | 1.5 | $p < 0.01$ |

The results show that both VE and VA produced the expected reduction of sebogenesis, however, at the tested dosages, VA (−29%) resulted as more effective than VE (<19%).

Conclusions

The experimental data attested that the main components of the valerian extract, i.e. valerenic acid and pentanoic acid, as well as the raw valerian root extract, are strong regulators of sebogenesis. The valerian extracts and their derivatives can therefore be exploited as ingredients for preparations aimed to reduce aesthetic problems such as oily skin, greasy hair and dandruff or for therapeutical treatments of skin diseases such as acne, seborroic dermatitis etc.

Examples 23-24 show that valerian extract is very active as sebogenesis inhibitor at 0.4-4 μg/ml (i.e. $0.4 \times 10^{-4}$%), therefore, according with the methological comments reported as introduction to the examples, the effective concentration in the cosmetic product could be 0.04-0.4%. However, since some active compounds, and in particular valepotriates and sesquiterpenes, undergo progressive oxidation and/or degradation, a concentration from 0.4 to 4% is recommended.

Examples 5-7 show that valerenic acid is very effective at 0.05-5 μM (i.e. $0.117\text{-}11.7 \times 10^{-5}$%), therefore, considering the multiplicative factor suggested for the formulation of a topical product, the final concentration at 0.00117-0.117% is recommended. Since the standard valerian extract contains about 0.3% in valerenic acid, the above suggested concentrations of valerenic acid can be obtained by adding 0.39-39% of valerian extract in the cosmetic preparation.

The experimental data obtained from treatments with valerian extract, as well as with valerenic acid, therefore suggest formulating effective compositions comprising about 0.04-40% valerian extract.

B. Activity of Valerian Extract and Their Derivatives on the Adipocyte Metabolism The reported examples from 19 to 23 are intended to show the modulation of adipocyte lipid content exerted by the experimental preparations on human skin subcutis. Full-thickness ex-vivo human skin samples, including the subcutis, were ex-vivo cultured and treated with compounds obtained from valerian extract, i.e. valerenic acid (VA) and pentanoic acid (AP), in order to evaluate their activity on the lipid metabolism.

The responses of the treated tissues, in comparison to the untreated group, were evaluated after 6 days of culture, by isolating the subcutis of each skin sample and then estimating its normalized content in total lipids.

Examples 28 to 32

Activity of Valerenic Acid (VA) and Pentanoic Acid (AP) on on the Lipid Metabolism of Full-Thickness Skin with Subcutis Cylindrical pieces (7 mm in diameter) of full thickness human skin were excised from an abdominal skin sample paying attention to preserve the subcutis. These organ samples were seeded in 24-well plates at a density of 1 sample/well with 500 μl of culture medium, and cultured up to day 6. The samples submitted to experimental treatments received medium supplemented with VA at 0.5, 5 and 50 μM or PA at 0.2 and 2 μM. After the first day of culture, the samples were arranged in experimental groups including 4 samples each one. The control group received modified William E medium, while the samples submitted to experimental treatments received the same medium supplemented with the extracts. The culture medium was renewed every other day. After six days of organ culture (five of treatment), the subcutis of each skin sample was separated from the dermis and its total content of lipids and proteins was quantified. The obtained content of lipids was normalized dividing it by the correlated content of proteins (mg lipids/mg proteins), in order to make the values detected in organ samples with different biomass comparable. In fact, stimulation of lipogenesis in the subcutis promotes synthesis and storage of lipids, while it does not substantially affect the metabolism of the structural proteins. As a result, when lipogenesis is stimulated, an increase in the "total lipids/total proteins ratio", hereinafter defined "normalized total lipids", is expected, while the contrary occurs in the case of increased lipolysis.

The analytical protocol adopted to detect values of "normalized total lipids" is described below:
  each subcutis sample was homogenized in 1 ml of isopropyl alcohol;
  the sample was centrifuged at 14,000 G for 5 minutes and then the supernatant (containing the extracted lipids) was collected;
  the supernatant was diluted 10 fold with isopropyl alcohol;
  the diluted lipid extract was analysed with a Direct Detect IR Spectrometer (Millipore), which provided the total lipid concentration of the supernatant (mg/ml);
  the total lipids of the subcutis sample was quantified multiplying the supernatant lipid concentration (indention 4) by the preliminary dilution factor (indention 3) and then by the volume of isopropyl alcohol used for the lipid extraction (indention 1);
  the residual pellet obtained from indention 2 was washed with 1 ml of isopropyl alcohol and, after another centrifugation this solvent was withdrawn;
  the pellet was dried in a vacuum dry evaporator and then homogenized in 100 ul of proteolytic buffer (20 mM Tris HCl pH 7.5, 150 mM NaCl, 2 mM EDTA, 0.5% Triton X-100, 2 mM DTT, 1% protease inhibitor cocktail);
  the extractive mixture was centrifuged at 14,000 G for 10 minutes and the supernatant was collected and analysed with a Direct Detect IR Spectrometer (Millipore), which provided the total protein concentration of the supernatant (mg/ml);
  the obtained total protein concentration was multiplied by the extractive volume (indention 7) in order to quantify the total proteins of the subcutis sample;
  the total lipids (indention 5) were divided by the total proteins (indention 9) in order to obtain the amount of lipids per mg of proteins relative to the processed subcutis sample.

Table 9 shows the normalized total lipids (total lipids/total proteins) of the experimental groups, expressed as percentage ratio of the control group performance.

TABLE 9

Total lipid content in skin subcutis samples following treatment with VA and PA. Responses expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 13.7 | |
| 0 | Capsaicin | 5 μM | 73.6 | 9.7 | p < 0.01 |
| 28 | VA | 0.5 μM | 63.9 | 6.5 | p < 0.05 |
| 29 | VA | 5.0 μM | 55.3 | 1.7 | p < 0.01 |
| 30 | VA | 50.0 μM | 59.0 | 3.6 | p < 0.01 |
| 31 | PA | 0.2 μM | 82.6 | 11.0 | n.s. |
| 32 | PA | 2.0 μM | 91.6 | 8.9 | n.s. | results attest that both the compounds reduced the lipid content in the skin subcutis. The more intense response (−44.7%) was detected following the treatments with VA 5.0 μM. Also PA produced a 17.8% reduction in total lipid content. These data show that the valerian extracts and their derivative compounds affect the metabolism of lipids and can be adopted for modulating the skin subcutis metabolism.

What is claimed is:

1. A method for treating scalp disorders caused by excessive sebogenesis, comprising topically administering on the scalp a composition comprising a valerian extract or an ester obtained from the combination of acid contained in the valerian extract with an aliphatic alcohol, in an amount effective for reducing sebum content, thereby treating the scalp disorders caused by the excessive sebogenesis.

2. The method according to claim 1, wherein the valerian extract or ester obtained from the combination of the acid contained in the valerian extract with aliphatic alcohol is administered in an amount of about 0.00004 to about 20% b.w.—calculated on the total composition.

3. A method for treating a subject suffering from disorder of hair and/or skin caused by excessive sebogenesis and/or sebaceous glands and/or hypodermal fat, comprising administering to the subject a composition comprising a valerian extract or an ester obtained from the combination of acid contained in the valerian extract with an aliphatic alcohol, in an amount effective for treatment of the disorder of hair and/or skin caused by excessive sebogenesis and/or sebaceous glands and/or hypodermal fat, wherein the valerian extract comprises pentanoic acid and/or valerenic acid, and comprising administering the composition to the subject in an amount effective for the treatment of dandruff.

4. The method according to claim 3, comprising topically or orally administering the extract or ester obtained from the combination of the acid contained in the valerian extract with aliphatic alcohol.

5. The method according to claim 3, wherein the valerian extract or ester obtained from the combination of the acid contained in the valerian extract with aliphatic alcohol is administered in an amount of about 0.00004 to about 20% b.w.—calculated on the total composition.

6. A method for treating a subject suffering from disorder of hair and/or skin caused by excessive sebogenesis and/or sebaceous glands and/or hypodermal fat, comprising administering to the subject a composition comprising a valerian extract or an ester obtained from the combination of acid contained in the valerian extract with an aliphatic alcohol, in an amount effective for treatment of the disorder of hair and/or skin caused by excessive sebogenesis and/or sebaceous glands and/or hypodermal fat, wherein the valerian extract comprises pentanoic acid and/or valerenic acid, and comprising administering the composition to the subject in an amount effective for the treatment of seborrhea.

7. The method according to claim 6, wherein the valerian extract or ester obtained from the combination of the acid contained in the valerian extract with aliphatic alcohol is administered in an amount of about 0.00004 to about 20% b.w.—calculated on the total composition.

8. The method according to claim 6, comprising topically or orally administering the extract or ester obtained from the combination of the acid contained in the valerian extract with aliphatic alcohol.

9. A method for treating scalp disorders caused by excessive sebogenesis, comprising topically administering on the scalp a composition comprising a valerian extract or an ester obtained from the combination of acid contained in the valerian extract with an aliphatic alcohol, in an amount effective for reducing sebum content, thereby treating the scalp disorders caused by the excessive sebogenesis, wherein the valerian extract comprises pentanoic acid and/or valerenic acid.

10. The method according to claim 9, wherein the valerian extract or ester obtained from the combination of the acid contained in the valerian extract with aliphatic alcohol is administered in an amount of about 0.00004 to about 20% b.w.—calculated on the total composition.

11. A method for treating a subject suffering from disorder of hair and/or skin caused by excessive sebogenesis and/or sebaceous glands and/or hypodermal fat, comprising administering to the subject a composition comprising a valerian extract or an ester obtained from the combination of acid contained in the valerian extract with an aliphatic alcohol, in an amount effective for treatment of the disorder of hair and/or skin caused by excessive sebogenesis and/or sebaceous glands and/or hypodermal fat, wherein the valerian extract comprises pentanoic acid and/or valerenic acid, and comprising administering the composition to the subject in an amount effective for the treatment of cellulite.

12. The method according to claim 11, wherein the valerian extract or ester obtained from the combination of the acid contained in the valerian extract with aliphatic alcohol is administered in an amount of about 0.00004 to about 20% b.w.—calculated on the total composition.

13. The method according to claim 11, comprising topically or orally administering the extract or ester obtained from the combination of the acid contained in the valerian extract with aliphatic alcohol.

* * * * *